United States Patent
Guala et al.

[11] Patent Number: 5,749,861
[45] Date of Patent: May 12, 1998

[54] CONNECTOR WITH PROTECTION VALVE FOR MEDICAL INFUSION/TRANSFUSION LINES AND THE LIKE

[75] Inventors: Ernesto Guala; Gianni Guala, both of Turin, Italy

[73] Assignee: Industrie Borla S.p.A., Turin, Italy

[21] Appl. No.: 806,418

[22] Filed: Feb. 26, 1997

[30] Foreign Application Priority Data

Feb. 26, 1996 [IT] Italy .................... TO96A0132

[51] Int. Cl.[6] ................................ A61M 5/00
[52] U.S. Cl. ............. 604/249; 604/256; 604/905; 251/149.1
[58] Field of Search ............... 604/246, 249, 604/905, 283, 256; 251/149.4, 149.1

[56] References Cited

U.S. PATENT DOCUMENTS

| | | |
|---|---|---|
| 5,242,423 | 9/1993 | Goodsir et al. |
| 5,390,898 | 2/1995 | Smedley et al. |
| 5,465,938 | 11/1995 | Werge et al. .................. 251/149.1 |
| 5,520,665 | 5/1996 | Fleetwood ....................... 604/283 |
| 5,535,771 | 7/1996 | Purdy et al. ....................... 137/15 |
| 5,569,235 | 10/1996 | Ross et al. ....................... 604/403 |
| 5,578,059 | 11/1996 | Patzer ............................. 604/249 |

FOREIGN PATENT DOCUMENTS

| | | |
|---|---|---|
| 0544581 | 6/1993 | European Pat. Off. |
| 0696460 | 2/1996 | European Pat. Off. |
| WO9317740 | 9/1993 | WIPO |
| WO9507720 | 3/1995 | WIPO |

Primary Examiner—Mark Bockelman
Assistant Examiner—Cris L. Rodriguez
Attorney, Agent, or Firm—Sughrue, Mion, Zinn, Macpeak & Seas, PLLC

[57] ABSTRACT

A connector for medical infusion/transfusion lines, catheters and the like, comprising a tubular body with a protection valve including an obturator formed by a resilient disk having a circumferential sealing edge normally co-operating under closing contact with an annular valve seat having a conical surface. On the side opposite to the annular valve seat, the obturator disk bears against an annular reaction surface of the body, and opening of the protection valve is operated by axial displacement of a tubular push member acting so as to press the central area of the obturator disk into the annular reaction surface thus elastically stretching it in the axial direction, whereby the circumferential sealing edge of the obturator disk radially retracts, moving away from the annular valve seat. (FIG. 4)

14 Claims, 6 Drawing Sheets

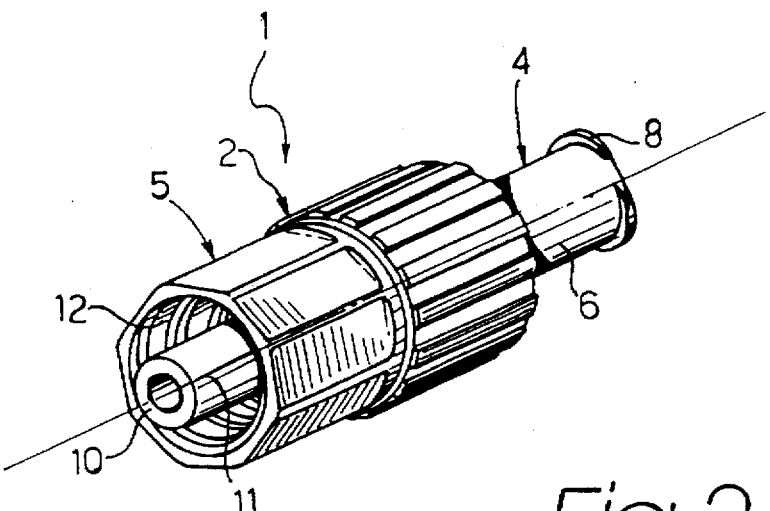
Fig_1
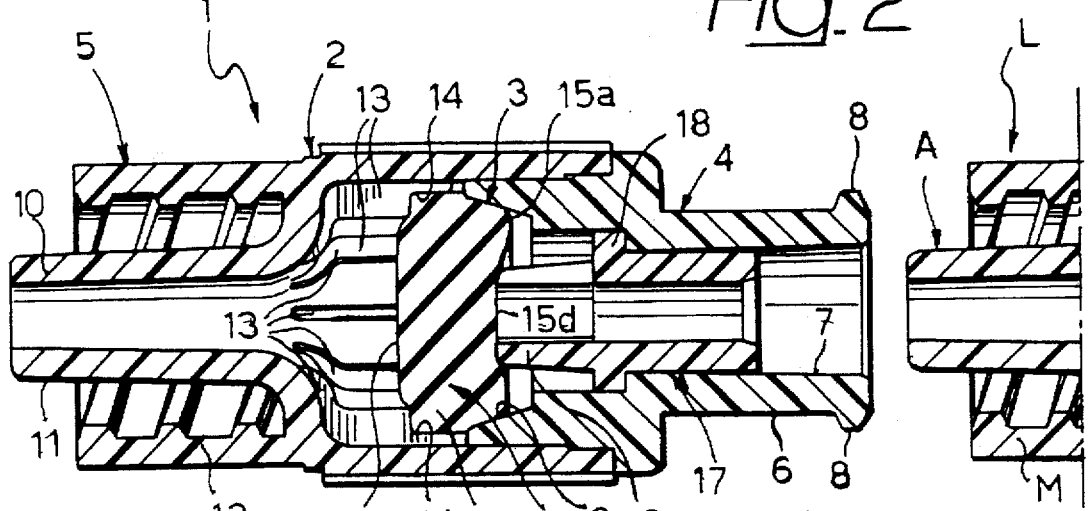
Fig_2
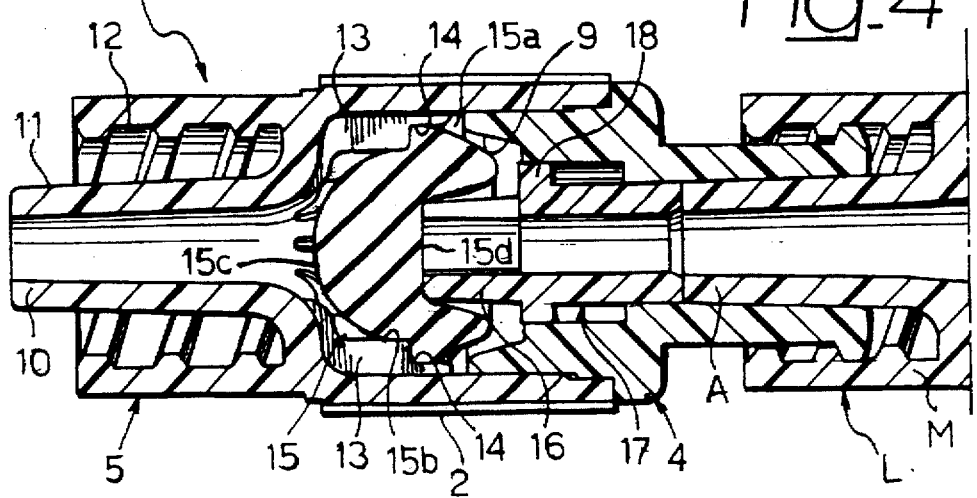
Fig_4

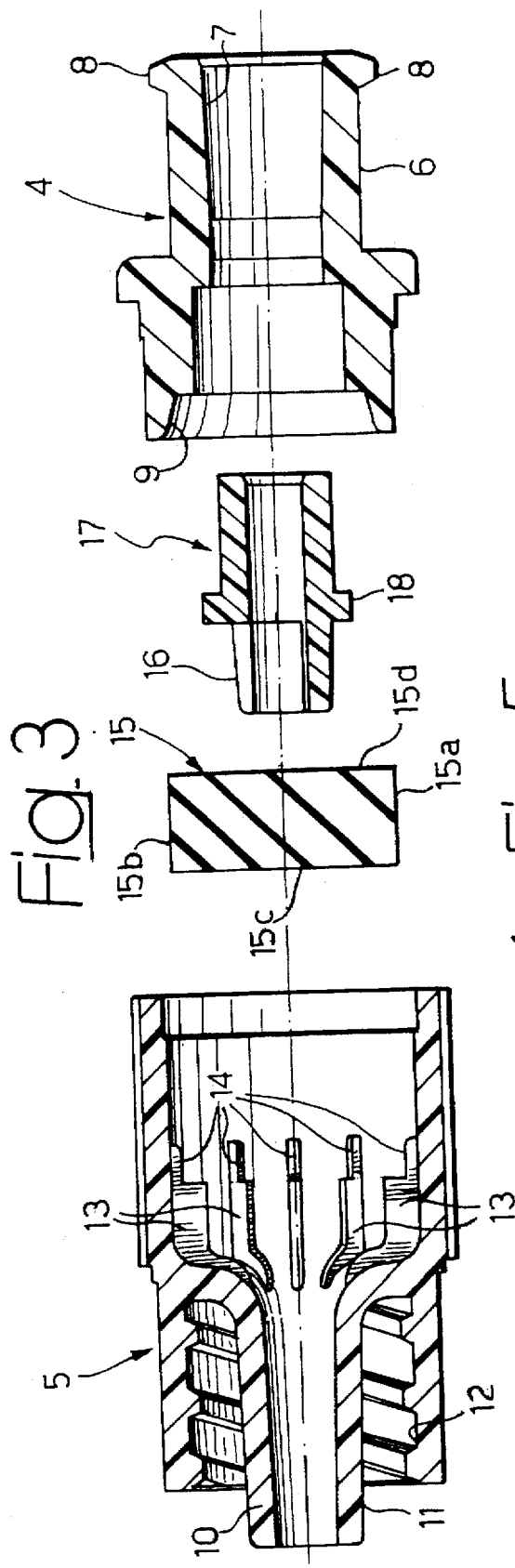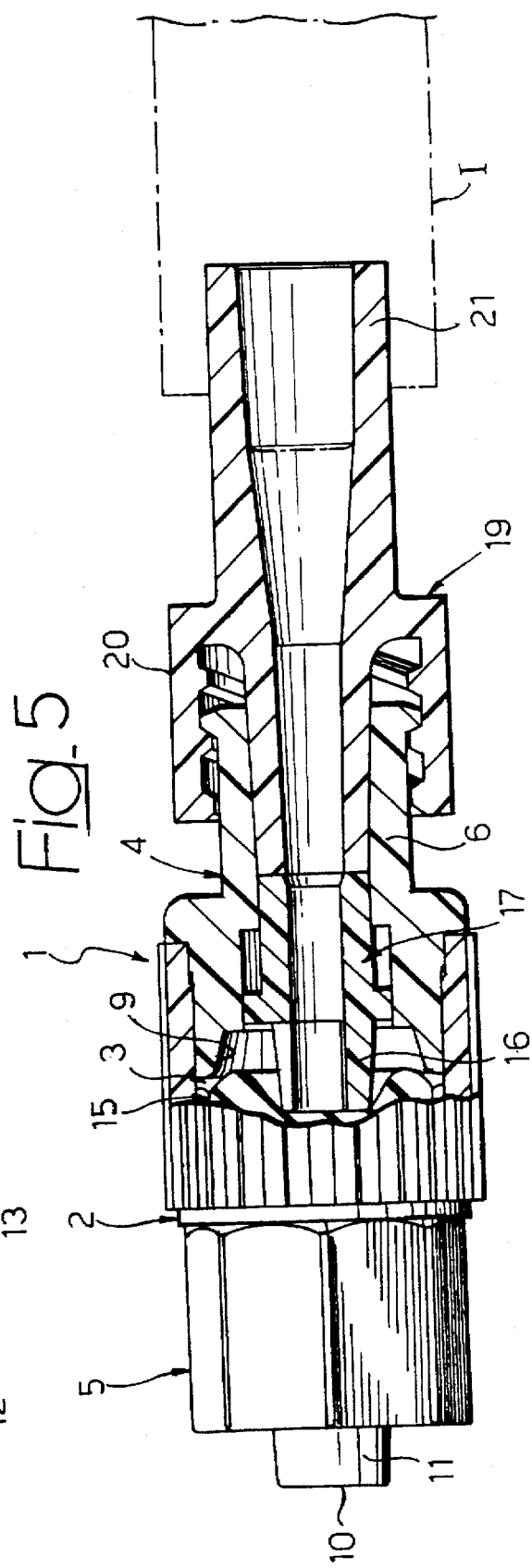

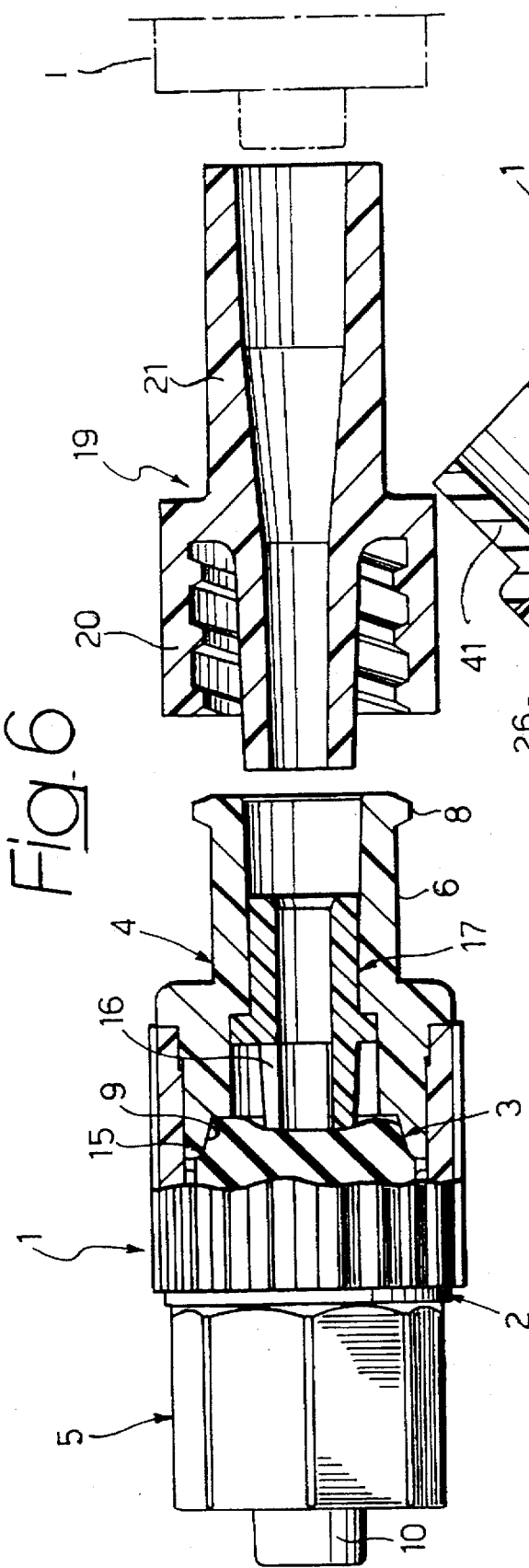
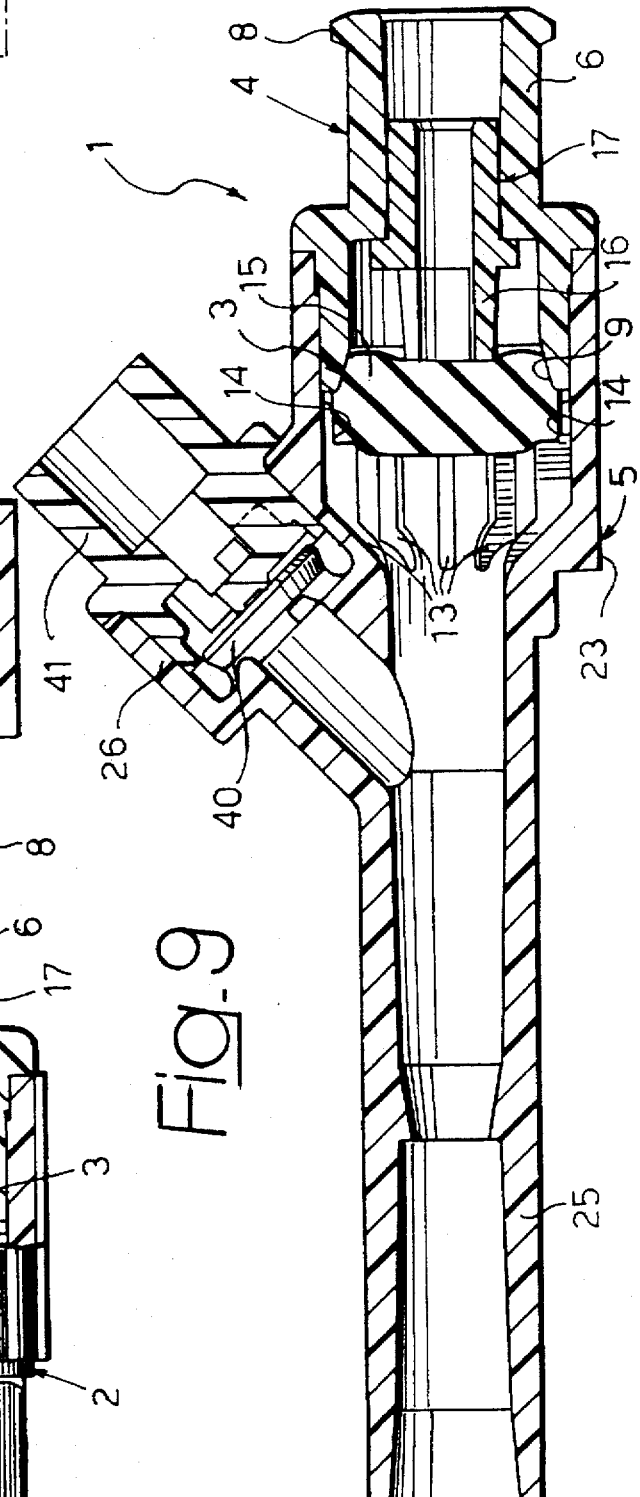
Fig. 6
Fig. 9

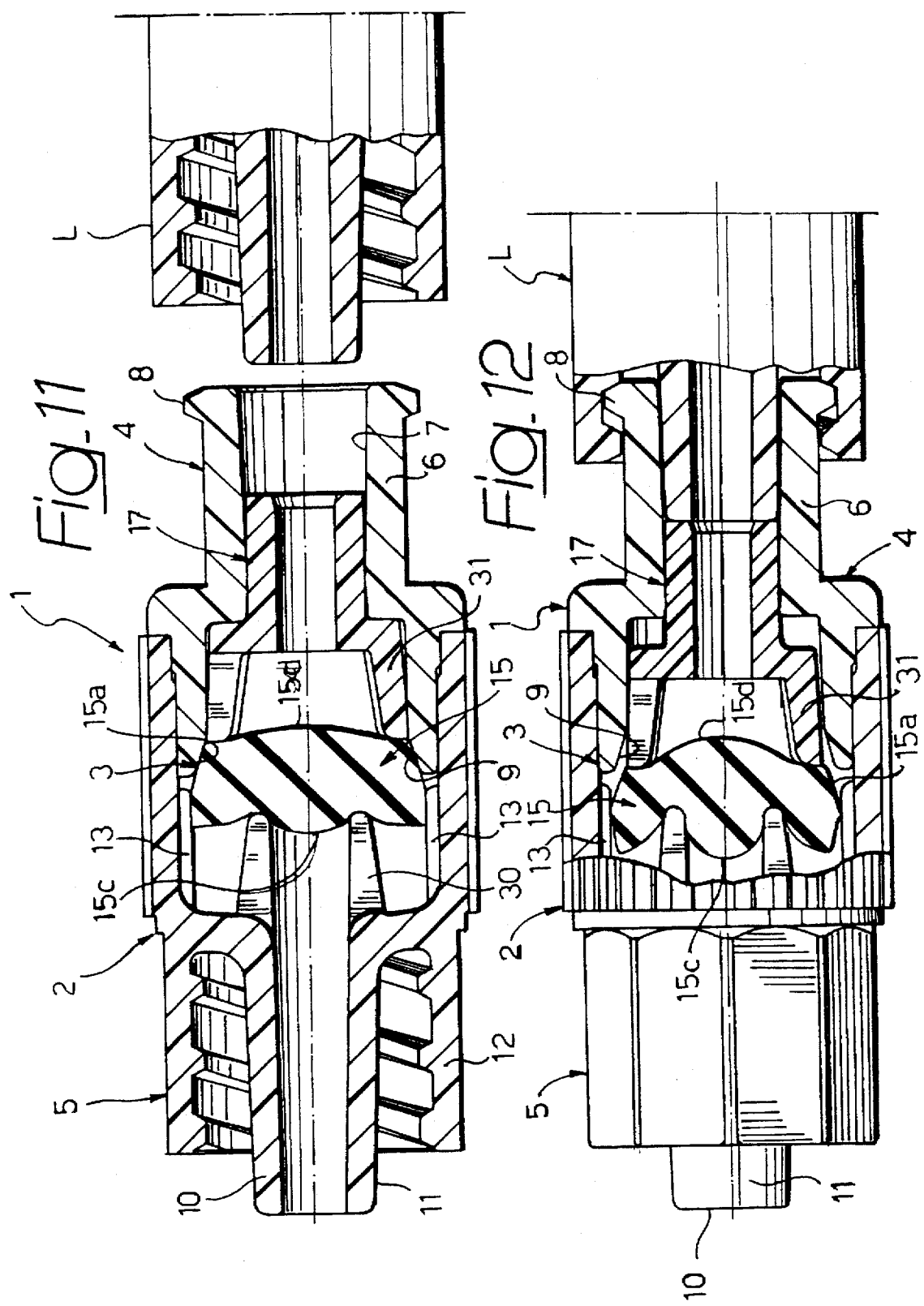

though reduced radial direction. Moreover, manufacturing is rather simple and unexpensive as well as the closing response of the valve is immediate and prompt, under any circumstances and conditions of use.

CONNECTOR WITH PROTECTION VALVE FOR MEDICAL INFUSION/TRANSFUSION LINES AND THE LIKE

BACKGROUND OF THE INVENTION

The present invention is generally related to connectors for medical use, intended to be employed as injection sites in infusion/transfusion lines, catheters, dialysis lines, volumetric sets and like application in the medical and also in the pharmaceutical field. These connectors are intended to enable introduction (or also extraction) of a fluid through a needle or needleless injection (or suction) member, to be coupled with the connector.

For safety reasons, these connectors have to be equipped with an inner protection valve allowing flow passage upon insertion of the injection (or suction) member, while sealingly closing the flow path when this injection (or suction) member is removed.

More particularly, the invention is directed to a connector for the above-listed applications, comprising a tubular body defining an axial flow path and having at one end an inlet fitting to axially receive the rein a fluid dispenser member, and an outlet at the other end thereof; an annular valve seat provided in said fluid path between the inlet fitting and the outlet, on the side of said inlet fitting; a valve obturator formed by a resilient member housed within the body transversally to said fluid path, on the side of said outlet, and having a peripheral circumferential sealing edge normally co-operating under closing contact with said annular valve seat to hermetically isolate the inlet fitting from the outlet; and tubular push means axially slidable within the body on the side of said inlet fitting from a retracted position to an advanced position to elastically strain said valve obturator, following axial introduction of the fluid dispenser member into the inlet fitting, so as to move said circumferential edge of the valve obturator away from said annular valve seat and open thereby communication between the inlet fitting and the outlet of the connector.

It is to be painted out that, in the following specification and claims, the term "fluid dispenser member" is intended to be generally referred to a syringe (either of the needle or needlelesss type) through which a fluid can not only be injected, but also withdrawn through the connector, as well as to any equivalent device.

A connector with protection valve of the above-referenced type is known, for instance, from U.S. Pat. No. 5,085,645 according to which the valve obturator is formed by an elongate bowl-like resilient member, having one end facing towards the inlet fitting and within which a push collar (which may also be formed integrally with the resilient bowl-like member) is conjugated, and whose opposite end is closed. When the fluid dispenser member is introduced into the connector inlet fitting, the resilient bowl-like member is strained by the push collar so as to collapse under axial compression. This bowl-like member is normally made of elastomeric material and since an annular gap is provided between its outer wall and the inner wall of the body, its axial contraction produces a radial expansion thereof. Accordingly, axial contraction determines moving the sealing edge in the axial direction away from the annular seat and, therefore, opening the valve so as to allow fluid passage from the dispenser member towards the outlet of the connector. The fluid flow towards the outlet is provided by means of inner channels formed in the body between the valve seat up to a distal portion thereof placed downstream of the closed end of the obturator bowl. Upon withdrawal of the dispenser member from the connector, resiliency of the obturator bowl provides axial return thereof to the underformed condition thereby closing the valve.

This construction, while being suitable to give a solution to a few problems related to the state of the prior art mentioned in the introduction of document U.S. Pat. No. 5,085,645, is still affected by a number of drawbacks.

Firstly the design of the valve obturator is constructively complicated and has a remarkable axial encumbrance, resulting into a relevant axial size of the connector as a whole. Even encumbrance of the connector in the radial direction is relatively large, in order to enable radial expansion of the resilient bowl, and its manufacturing is difficult also due to the presence of the flow channels formed at the outside of the bowl itself. As a consequence, the inner volume of the connector is relatively large, which produces useless and undesired fluid storage therewithin, as well as within the cavity of the obturator bowl. On the other hand, even due to the relevant axial size of the obturator bowl, return thereof to the undeformed closing condition following withdrawal of the fluid dispenser member from the connector is not as prompt and immediate as it would on the contrary be desirable, with the risks which may derive thereby. For instance, in the case of application to a catheter there may be a danger of blood leakage which, if infected, may spread contagion.

SUMMARY OF THE INVENTION

The object of the present invention is to overcome these inconveniences, and more particularly to provide a connector with protection valve of the type set forth in the above having a remarkably more simple hand unexpensive construction, as well as reduced axial and radial size.

A further object of the invention is to provide a connector with protection valve of the type set forth in the above which can warrant an almost immediate closing of the valve upon withdrawal of the fluid dispenser member, without any possibility of undesired fluid flow back.

A further object of the invention is to provide a connector with protection valve of the type set forth in the above which is adapted to be indifferently employed with fluid dispenser members both of the needle and of the needleless type.

Still a further object of the invention is to provide a connector with protection valve of the type set forth in the above which is adapted to be used to advantage in a number of different constructive embodiments and applications in the medical and also in the pharmaceutical field, including providing injection sites in covers and caps of bottles and the like for pharmaceutical products including components to be mixtured together.

In view to achieve the above objects, the present invention is related to a connector with protection valve of the type defined at the beginning, the primary feature of which resides in that the valve obturator has a generally solid disk configuration; the connector body has an annular reaction surface juxtaposed and adjacent to said annular valve seat and against which said obturator disk bears on the side of said outlet; and said tubular push means act, in said advanced position, so as to press said obturator disk into said annular reaction surface thus elastically stretching it in the axial direction towards said outlet, whereby said circumferential sealing edge of the obturator disk radially retracts, moving away from said annular valve seat.

By virtue of this idea of solution, the connector according to the invention has a reduced and particularly compact configuration both in the axial direction and even in the radial direction, and manufacturing thereof is made simple and unexpensive also in consideration of the elementary construction of the valve disk obturator. This elementary structure also ensures a perfect fluid tightness in the closed condition of the valve, an easy opening thereof upon introduction of the fluid dispenser member into the connector, as well as a prompt and immediate return to the closed condition following withdrawal of this dispenser member. Additionally, the disk obturator is easily pierceable by a needle of the dispenser member if so provided, upon axial introduction thereof along the connector body.

According to a first embodiment of the invention, which is to be considered as the preferred one, said annular reaction surface of the connector body is defined by a crown of axial ribs integrally formed with the body and against which the peripheral area of the obturator disk is back resting, said ribs defining flow channels communicating with said outlet, and the tubular push means comprise a grooved sleeve guided along said inlet fitting and frontally abutting against the central area of the obturator disk.

According to a variant of the invention, the annular reaction surface is defined by an inner grooved tubular appendage integrally formed with the body coaxially to said outlet and against which the central area of said obturator disk is back resting, and the tubular push means comprise a grooved sleeve guided along said inlet fitting and frontally abutting against the peripheral area of said obturator disk.

Additional features and advantages of the invention will become apparent through the following detailed description, with reference to the accompanying drawings purely provided by way of non limiting example, in which:

BRIEF DESCRIPTION OF THE DRAWING

FIG. 1 is a diagrammatic perspective view of a connector with protection valve according to a first embodiment of the invention, FIG. 2 is a longitudinally sectioned and enlarged view of the connector of FIG. 1, showing the protection valve in the closed position, FIG. 3 is an exploded view of FIG. 2, FIG. 4 is a view similar to FIG. 2 with the protection valve in the open position, FIG. 5 is a view similar to FIG. 2 showing an adapter member which may be associated to the connector according to the invention, FIG. 6 is an exploded view of FIG. 5, FIG. 9 is a longitudinally sectioned view showing a second alternative application of the connector according to FIG. 1, FIG. 11 is a view similar to FIG. 2 showing a variant of the connector according to the invention with the protection valve in the closed position, and FIG. 12 is a view similar to FIG. 11 with the protection valve in the open position.

DESCRIPTION OF THE PREFERRED EMBODIMENTS

Figure 7:
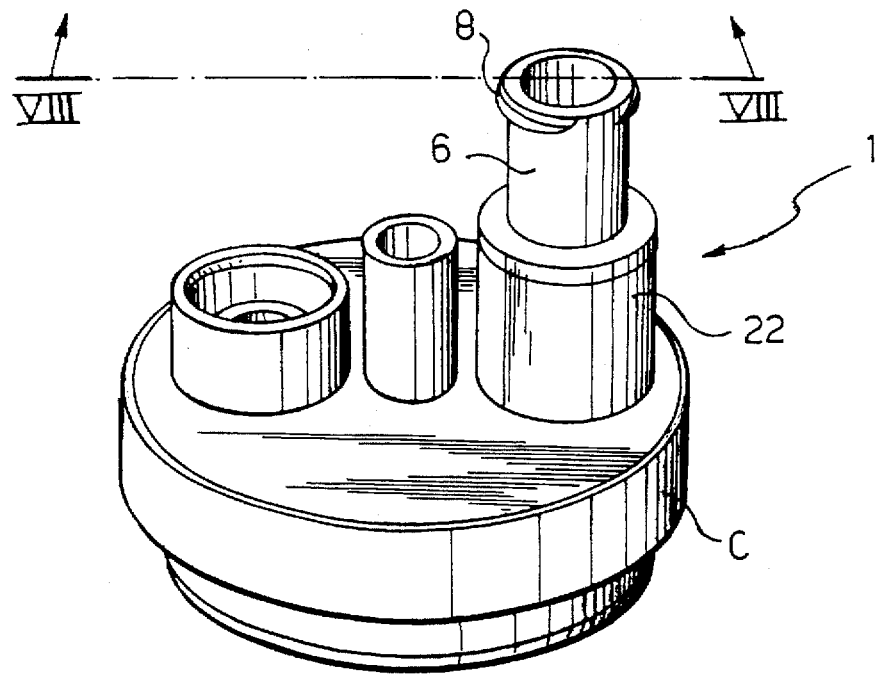
FIG. 7 is a perspective view showing a first alternative application of the connector according to FIG. 1.

Referring initially to FIGS. 1 through 3, reference numeral 1 generally designated a connector according to the invention for medical infusion/transfusion lines and catheters, conventionally designated as "eparin lock".

The connector 1 is formed by a tubular body 2 defining an axial flow path through which a protection or check valve, generally indicated as 3, is fitted.

The body 1 is comprised of a first section or inlet section 4 made of moulded plastic material (compatible with physiological solution, pharmaceuticals and haemo-derivatives), and by a second section or outlet section 5 made of the same material, coaxial with each other and of which the former is rigidly and permanently joined within the latter, for instance by bonding, ultra-sound welding or similar systems.

The inlet section 4 is designed at one side as a female luer lock fitting 6, with a slightly conical inner surface 7 converging towards the interior of the connector 1, and helical outer projections 8. On the other side, i.e. in its axial portion engaged into the second section 5, section 4 is formed at its inner end with an annular seat 9 having a conical surface diverging towards the second section 5.

The second section 5 is formed on one side with a male luer lock fitting comprising in a conventional way a tubular appendage 10 having a slightly conical outer surface 11 and partially surrounded coaxially by an innerly threaded cylindrical wall whose outer surface is normally polygonal. On the other side, i.e. the one facing towards the first section 4, the second section 5 is innerly formed with a crown of axial ribs 13 whose outer ends smoothly merge into the tubular appendage 10 and whose inner ends are shaped like steps 14 frontally facing towards the conical surface annular seat 9.

Reference 15 designates a disk made of a resilient material (latex, elastomer, polyisoprene, silicone rubber and the like). As shown in FIG. 3, the resilient disk 15 has in its undeformed condition an elementary solid cylindrical shape with a generally circular cross section, and its radial size is greater then its axial size. In the assembled condition within the body 2 of the connector 1, the resilient disk 15 is circumeferentially held between section 4 and section 5. More particularly, an axial portion of the lateral surface of the disk 15, indicated as 15a and placed on the side of the first section 4, is normally maintained under hermetic closing contact against the conical surface annular seat 9. An adjacent axial portion of the lateral surface of the resilient disk 15, indicated as 15b and facing towards the first section 5, bears against the step portions 14 of the ribs 13, together with the adjacent circumferential area of the rear wall 15c of the disk 15.

Against the central area of the front wall of the disk 15, indicated as 15d, the front grooved end 16 of a tubular push member 17 is abutting, which has a sleeve-like design and is slidably guided within the fitting 6 of the first section 4. The tubular push member 17 has a substantially central annular collar 18 acting as an axial stop element relative to the fitting 6.

The resilient disk 15 and the annular seat 9 define the protection valve 3: FIG. 2 shows this valve 3 in the closed condition, in which the obturator constituted by the resilient disk 15 is slightly clamped in the back and in the front between the steps 14 and the grooved end 16 of the tubular push member 17, respectively, with it circumferential portion 15a placed under hermetic closure contact against the annular seat 9. Flow passage from section 4 (through the cavity of the fitting 6, the cavity of the tubular push member 17 and the end grooves 16 thereof) towards the second section 5 (through the channels defined by the ribs 13 and the cavity of the tubular appendage 10) is thus prevented by the protection valve 3.

In use, the male luer lock fitting formed by the section 5 of the body 2 is connected to a complementary female luer lock fitting in turn connected to an infusion/transfusion line, to a catheter or the like, so as to provide a fluid injection (or extraction) site. In order to inject (or withdraw) the fluid, the female luer lock fitting formed by the first section 4 of the body 2 is thus connected to a dispenser member for instance constituted by a syringe or the like. In case the syringe or the like is of the needle type, this needle is introduced along the connector 1, piercing the resilient obturator disk 15. Following injection of the fluid and subsequent withdrawal of the syringe needle, the inherent elasticity of the disk 15 promptly re-establishes closure of the flow path through the connector 1.

In case the fluid dispenser member is of the needleless types operation is as follows.

FIGS. 2 and 4 diagrammatically show, in the right side, the tip end of such a needleless fluid dispenser member, in the specific case same is provided—in a way known per se—with a male luer lock fitting, generally designated as L, formed by an innerly threaded cylindrical wall M and by a tubular appendage A extending coaxially therein and axially projecting therefrom.

In this case, when the male luer lock fitting L of the dispenser member is fitted into and engaged relative to the female luer lock fitting 6 of the section 4 of the connector 1, the projecting tip of the tubular appendage A axially urges the tubular push member 17 in the direction of the section 5, which thus axially presses with its grooved end 16 against the central area of the front wall 15d of the resilient obturator disk 15. Consequently, and as illustrated in FIG. 4, the obturator disk 15 is elastically deformed and axially stretched within the steps 14 and, to a more or less relevant degree, within the crown of ribs 13. Since elastic deformation of the obturator disk 15 takes place under constant volume thereof, its central axial extension causes a radial retraction of its lateral surface, whereby the circumferential area 15a moves away from the annular seat 9 so as to open the protection valve 3. The flow passage between the sections 4 and 5 of the body 2 of the connector 1 is thus enabled in order to allow the fluid injected by the dispenser member to flow, along the channels defined by the ribs 13, into the tubular appendage 10 and to the line associated to the connector 1.

At the end of this operation, withdrawal of the dispenser member causes prompt and immediate elastic return of the disk obturator 15 to the undeformed start position of FIG. 2, thus performing instantaneous closing again of the protection valve 3, without any risks of undesired flow back of the fluid from section 5 to section 4 of the connector 1.

In case the dispenser member is not provided with a male luer lock fitting as in the example disclosed in the above, the invention contemplates the provision of an intermediate tubular adapter member 19, depicted in FIGS. 5 and 6, in which parts which are identical or similar to those already previously disclosed are designated by the same reference numerals. The adapter member 19 is formed at one end like a male luer lock fitting 20, almost identical to the male luer lock fitting L disclosed in the above, and is provided at the opposite end with a female luer fitting 21 to be simply press-engaged axially by the corresponding end of the dispenser member, diagrammatically shown as I.

Accordingly, in use, the dispenser member I is firstly connected to the adapter member 19, and thus the male luer lock fitting 20 thereof is connected to the female luer lock fitting 6 of the section 4 of the connector 1, so as to operate opening of the protection valve 3 in the same identical way as previously disclosed.

The connector with protection valve according to the invention can be employed in a number of applications different from the one disclosed hereinbefore, some of which are shown by way of example in FIGS. 7 through 10. Even in these figures parts identical or similar to those previously disclosed are indicated by the same reference numerals.

Figure 8:
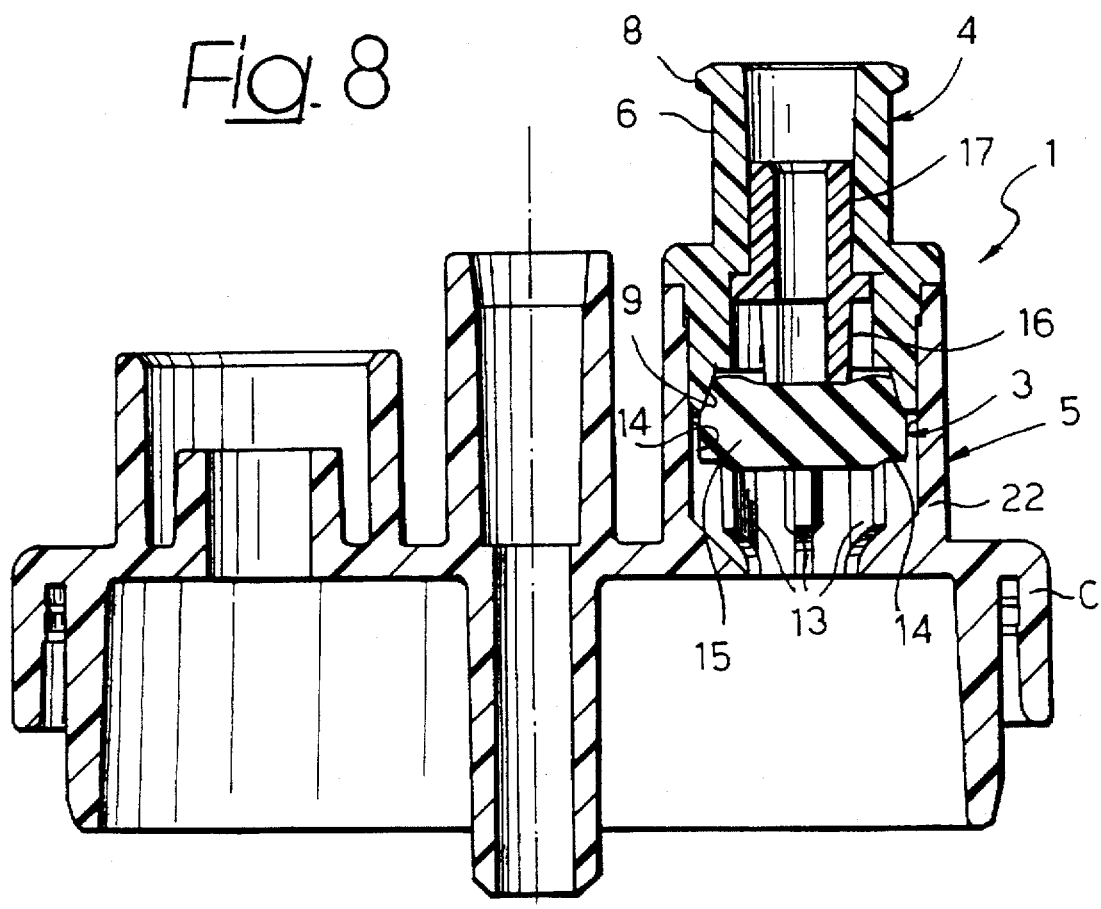
FIG. 8 is a sectioned and enlarged view along line VIII—VIII of FIG. 7.

FIGS. 7 and 8 show application of the connector 1 as an injection site for a volumetric set, and namely for a buret having a cover generally designated as C. In this case the section 5 of the connector 1, instead of being formed like a male luer lock fitting as in the case disclosed in the above, is simply constituted by a generally cylindrical body 22 integrally formed by moulding with the cover C, together with the related inner ribs 13. The configuration of the protection valve 3 and operation thereof are identical to those already previously disclosed.

FIG. 9 shows application of the connector 1 to a Y fitting for infusion/transfusion sets. In this case the section 5 of the body 2 is formed by a generally cylindrical body 23 which is integrally moulded, together with the related inner axial ribs 13, with an elongated axial duct and an oblique lateral duct 26. The oblique duct 26 may be provided with a check valve 40, formed by a resilient disk obturator known per se, axially retained by means of a connector 41 axially coupled and fixed relative to the oblique duct 26. Even in this case the arrangement and operation of the protection valve 3 are identical to those disclosed in the above.

Figure 10:
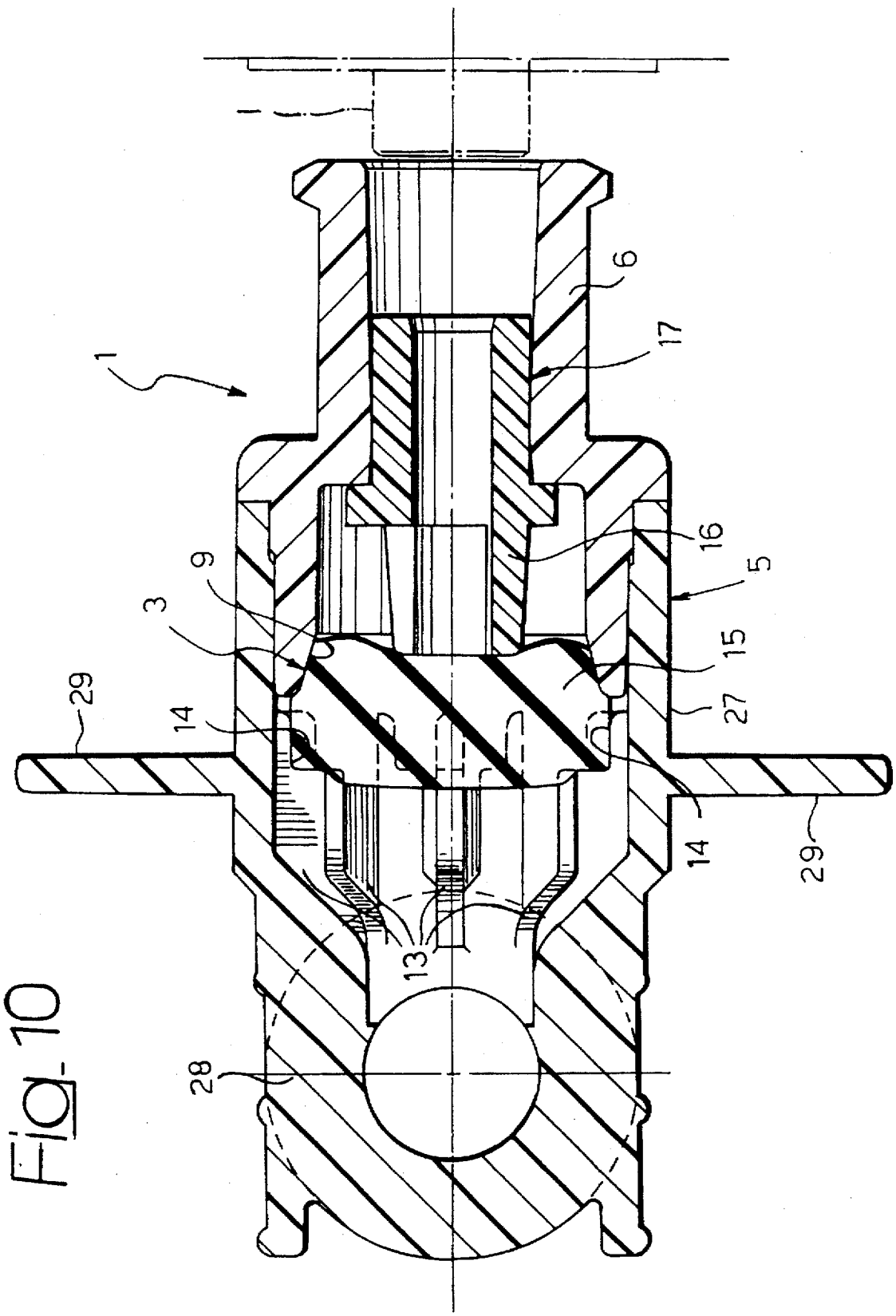
FIG. 10 is a longitudinally sectioned view showing a third alternative application of the connector according to FIG. 1.

In the case of FIG. 10 the connector 1 is applied to a cross fitting for dialysis lines. The section 5 is constituted by a generally cylindrical body 27 integrally moulded with a transverse tubular element 28 and outer shield wings 29. Again the arrangement and operation of the protection valve 3 are identical to those already disclosed.

It is to be pointed out that the connector 1 according to the invention may be employed in a number of further application other than those disclosed in the above, for instance has an injection site for flexible bags, and even in fields different from the medical one. A particularly advantageous possible application may consist, for instance, of associating the connector 1 to the cover of a bottle containing pharmaceutical substances intended to be mixtured with other liquid components which shall be introduced into the bottle through a dispenser member with or without needle.

FIGS. 11 and 12 show a variant of the connector with protection valve according to the invention. This variant, in which part which are identical or similar to those already previously disclosed are also indicated by the same reference numerals, differs from the preceding embodiment solely as far as arrangement of the protection valve 3 is concerned. In this variant, the steps 14 of the axial ribs 13 are suppressed, and the rear wall 15c of the obturator disk 15 centrally bears against an inner grooved tubular appendage 30 integrally formed with the section 5 of the body 2 and projecting, along the prolongation of the tubular appendage 10, towards the section 4. The inner grooved end of the tubular push member 17, indicated as 31, has a larger diameter with respect to that of the grooved end 16 of the previously disclosed embodiment, and abuts against the peripheral area of the front face 15d of the obturator disk 15, instead of against the central area thereof as in the previous case.

FIG. 11 shows the closed condition of the protection valve 3, in the absence of the fluid dispenser member. In this condition the circumferential surface 15a of the obturator disk 15 is kept under hermetic seal contact against the conical surface annular seat 9, whereby flow passage between the section 4 and the section 5 of the connector 1 is prevented.

Following insertion of the needleless fluid dispenser member, for instance including a male luer lock fitting L as in the case of FIGS. 2 through 4, the tubular push member 17 is axially displaced towards the section 5 of the body 2, thus pressing the obturator disk 15 against the tubular appendage 30. Consequently, the central area of the obturator disk 15 is "extruded", i.e. elastically stretched in the axial direction into the tubular appendage 30, thus determining the radial retraction of the peripheral area of the obturator disk 15, and consequently moving its circumferential surface 15a away from the annular seat 9. Further to in the axial direction, this movement away takes place also in the axial direction, owing to the strain produced against the peripheral area of the front wall 15d of the obturator disk 15 by the grooved end 31 of the tubular push member 17. The protection valve 3 is accordingly opened, thus allowing the flow of the fluid injected by the dispenser member through the cavity of the tubular push member 17, the grooved end 31 thereof, the passages defined by the axial ribs 13, the grooved appendage 30 and the tubular appendage 10.

Of course the variant of FIGS. 11 and 12 may be employed in all the application previously disclosed with reference to the first embodiment of the invention.

In summary, the principle of the present invention consists of using a valve obturator (the resilient disk 15) having an elementary geometric configuration with a substantial thickness but extremely reduced radial and axial size, and whose elastic deformation to operate opening of the protection valve is performed through an axial stretching of its central area, due to which a radial retraction of its peripheral area is carried out. This arrangement of the obturator disk 15 enables the whole connector 1 to be manufactured with reduced axial and radial sizes, thus reducing the inner volume thereof, while ensuring a pront and almost instantaneous return of the protection valve to the closed condition upon withdrawal of the fluid dispenser member from the connector.

Naturally the details of construction and the embodiments may be widely varied with respect to what has been disclosed and illustrated, without thereby departing from the scope of the present invention such as defined in the appended claims.

What is claimed is:

1. A connector for medical infusion/transfusion lines and the like, comprising a tubular body having first and second ends between which an axial flow path is defined, said body having at said first end an inlet fitting to axially receive therein a fluid dispenser member, and having an outlet at said second end thereof; an annular valve seat provided in said fluid path between said inlet fitting and said outlet, on the side of said inlet fitting; a valve obturator including a resilient member housed within the body transversally to said fluid path, on the side of said outlet, and having a peripheral circumferential sealing edge normally co-operating under closing contact with said annular valve seat to hermetically isolate said inlet fitting from said outlet; and tubular push means axially slidable within the body on the side of said inlet fitting from a retracted position to an advanced position to elastically strain said valve obturator, following axial introduction of said fluid dispenser member into said inlet fitting, so as to move said circumferential edge of the valve obturator away from said annular valve seat and open thereby communication between said inlet fitting and said outlet, wherein:

said valve obturator has a generally solid disk configuration, said connector body has an annular reaction surface juxtaposed and adjacent to said annular valve seat and against which said obturator disk bears on the side of said outlet, said tubular push means operate, in said advanced position, so as to press said obturator disk into said annular reaction surface thus elastically stretching said obturator disk in the axial direction towards said outlet, whereby said circumferential sealing edge of said obturator disk radially retracts moving away from said annular valve seat.

2. Connector according to claim 1, wherein said obturator disk has a peripheral area and a central area, and said annular reaction surface is defined by a crown of axial ribs integrally formed within the body and against which said peripheral area of said obturator disk is back resting, said ribs defining flow channels communicating with said outlet, and wherein said tubular push means comprise a grooved sleeve guided along said inlet fitting and frontally abutting against said central area of said obturator disk.

3. Connector according to claim 1, wherein wherein said obturator disk has a peripheral area and a central area, and said annular reaction surface is defined by an inner grooved tubular appendage integrally formed with the body coaxially to said outlet and against which said central area of said obturator disk is back resting, and wherein said tubular push means comprise a grooved sleeve guided along said inlet fitting and frontally abutting against said peripheral area of said obturator disk.

4. Connector according to claim 1, wherein said inlet fitting is a female luer lock fitting to be engaged by a complementary male luer lock fitting of said fluid dispenser member.

5. Connector according to claim 1 wherein said inlet fitting is a female luer lock fitting and further comprising an intermediate tubular adapter member formed at one end thereof with a male luer lock fitting to be coupled with said female luer lock fitting, and at the other end thereof with a female luer fitting engageable by a complementary male luer fitting of said fluid dispenser member.

6. Connector according to claim 1, wherein said body comprises a first and a second sections of which the first section is integrally formed with said inlet fitting and with said annular seat valve, and the second section is integrally formed with said outlet and with said annular reaction surface, said first and second sections being permanently joined to each other coaxially, with said obturator disk being axially held between said annular valve seat and said annular reaction surface.

7. Connector according to claim 1, wherein said outlet comprises a male luer lock fitting.

8. Connector according to claim 1, wherein said outlet is defined by a Y fitting for catheter or infusion/transfusion set.

9. Connector according to claim 1, wherein said outlet is defined by an eparin lock for catheter or infusion/transfusion set.

10. Connector according to claim 1, wherein said outlet is defined by a cross fitting for catheter or dialysis line.

11. Connector according to claim 1, wherein said outlet is defined by an injection site for volumetric sets such as burets and the like.

12. Connector according to claim 11, wherein it is integrally formed with a buret cover.

13. Connector according to claim 1, wherein said outlet is applied to a pharmaceutical container cover.

14. Connector according to claim 1, wherein said disk obturator is pierceable by needle means to be axially introduced along said connector body.

* * * * *